United States Patent [19]

Boesten et al.

[11] Patent Number: 5,047,585

[45] Date of Patent: Sep. 10, 1991

[54] PROCESS FOR RACEMIZING AN OPTICALLY ACTIVE N-BENZYLIDENE AMINO-ACID AMIDE

[75] Inventors: Wilhelmus H. J. Boesten, Sittard; Hans E. Schoemaker, Urmond; Bernardus H. N. Dassen, Heerlen, all of Netherlands

[73] Assignee: Stamicarbon B.V., Geleen, Netherlands

[21] Appl. No.: 332,576

[22] Filed: Apr. 3, 1989

Related U.S. Application Data

[62] Division of Ser. No. 850,157, Apr. 10, 1986, Pat. No. 4,847,412.

[30] Foreign Application Priority Data

Apr. 12, 1985 [NL] Netherlands ............ 8501093

[51] Int. Cl.$^5$ ............................................. C07C 231/06
[52] U.S. Cl. ................................. 564/124; 435/280; 548/344; 548/491; 564/123; 564/160; 564/164; 564/165; 564/302; 564/198
[58] Field of Search ..................... 564/124, 302

[56] References Cited

U.S. PATENT DOCUMENTS 2,945,883 7/1960 Alberti et al. ............... 564/302
4,847,412 7/1989 Boesten et al. .............. 564/164

FOREIGN PATENT DOCUMENTS 1548032 7/1979 United Kingdom ........ 564/124

OTHER PUBLICATIONS

Boesten, W. et al., "Racemizing an Optically Active N-Benzylidene Amino Acid Amide", CA 107, 40327w, 1987.

Sakashita, K. et al., "Base-Catalyzed Racemization of α-Amino Acid Amides", CA 109, 73906d, 1988.

Primary Examiner—Richard L. Raymond
Assistant Examiner—Susan P. Treanor
Attorney, Agent, or Firm—Cushman, Darby & Cushman

[57] ABSTRACT

The invention relates to a process for racemizing an optically active N-benzylidene amino-acid amide, characterized in that a solution of the N-benzylidene amino-acid amide is mixed in a water-miscible organic solvent with at least 0.05 mole strong base per liter solution.

The invention further relates to a process for preparing an L-amino acid by enzymatic separation of the corresponding DL-amino-acid amide with an enzyme preparation from *Pseudomonas putida*, in which process also uncoverted D-amino-acid amide is left behind in solution, characterized in that benzaldehyde is added to the solution, during which addition a precipitate of D-N-benzylidene amino-acid amide is being formed, this precipitate is subsequently, after being separated off, dissolved in an acetone-water mixture, 0.08–0.15 mole KOH/liter solution is subsequently added, the resulting solution is stirred for 1–20 hours at 20°–60° C., sulphuric acid is then added until the pH of the solution is 5 and the resulting sulphuric acid salt of the DL-amino-acid amide is finally, after isolation at pH 8–10, converted into the DL-amino-acid amide and this DL-amino-acid amide is used again.

1 Claim, No Drawings

PROCESS FOR RACEMIZING AN OPTICALLY ACTIVE N-BENZYLIDENE AMINO-ACID AMIDE

This is a division of application Ser. No. 06/850,157, filed Apr. 10, 1986, now U.S. Pat. No. 4,847,412.

The invention relates to a process for racemizing an optically active N-benzylidene amino-acid amide. Such a process is not known. The invention also relates to a process for racemizing an optically active amino-acid amide.

For a correct insight into the process according to the invention first a number of definitions will now be given. An optically active amino acid, optically active amino-acid amide, optically active N-benzylidene amino-acid amide and optically active Schiff base of an amino-acid amide are in this connection understood to mean an amino acid, amino-acid amide, N-benzylidene amino-acid amide respectively Schiff base of an amino-acid amide with an asymmetric carbon atom at the α-position and in which there is an excess of one of the optical antipodes in respect of the other. When here and hereinafter the term Schiff base of an amino-acid amide is used, it is meant to denote the same compound as N-benzylidene amino-acid amide.

There is a strong need of a process as described in the opening lines. The fact is that from U.S. application Nos. 3,971,700 and 4,080,259 it is known how to prepare L-phenylglycine from DL-phenylglycine amide by means of selective enzymatic hydrolysis. However, in that process unconverted D-phenylglycine amide will remain in the hydrolysate also.

Economically it is necessary to have a process by which the undesired optical antipode of an amino-acid amide (in the case described above D-phenylglycine amide) can be racemized in order thus to make it possible for half of the starting material for the enzymatic hydrolysis to be recovered.

Applicant has now found that this racemization can be effected very advantageously through the formation of a Schiff base. For a major advantage is that then, according to, for instance, the process of U.S. application No. 4172846, the said L-phenylglycine and D-phenylglycine amide can first be separated, without racemization, by means of the formation of a Schiff base and the same Schiff base of D-phenylglycine amide can then be racemized.

According to the invention an optically active N-benzylidene amino-acid amide is racemized characterized in that a solution of the N-benzylidene amino-acid amide in a water-miscible organic solvent is mixed with at least 0.05 mole strong base per liter solution.

According to a particular mode of realizing the invention an optically active amino-acid amide is racemized by converting it into an optically active N-benzylidene amino-acid amide and racemizing the latter as mentioned above and converting the resulting racemic mixture into the DL-amino-acid amide.

Preference is given to preparing a DL-amino-acid amide from an optically active amino-acid amide in that the optically active amino-acid amide is converted into the corresponding optically active N-benzylidene amino-acid amide, a solution of the N-benzylidene amino-acid amide in a water-miscible organic solvent is mixed with at least 0.05 mole strong base per liter solution, this solution is subsequently brought to pH 3-7 by the addition of acid and finally the resulting salt of the DL-amino-acid amide is converted in an aqueous environment at pH 8-10 into the DL-amino-acid amide. Thus racemization of optically active N-benzylidene amino-acid amides and their subsequent conversion into the corresponding DL-amino-acid amides can be achieved very elegantly under relatively mild reaction conditions.

The process according to the invention can in principle be applied with all optically active N-benzylidene amino-acid amides.

Generally an optically active N-benzylidene amino-acid amide is prepared by converting benzaldehyde with an optically active amino-acid amide. The preparation of such compounds can be effected as described in U.S. application No. 4,172,846. According to U.S. application No. 4,172,846 the benzaldehyde may be substituted with, for instance, a hydroxyl group, nitro group, halogen, alkyl group with 1-6 C atoms, alkoxy group with 1-6 C atoms and a hydroxyalkyl group with 1-6 C atoms. It is stated in U.S. application No. 4,172,846 that in principle aldehydes and ketones other than benzaldehyde can also be used as imine-forming agents, but that preference is given to benzaldehyde. Therefore, whenever here and hereinafter the term N-benzylidene is used, it is understood also to include substituted N-benzylidene compounds, the substituents of which may be the same as described in U.S. application No. 4,172,846. However, other substituents can be used also. A wide variation in amino-acid amides, however, is also possible. Thus, for instance, the N-benzylidene derivatives of optically active phenylalanine, 3,4-dihydroxyphenylalanine, homophenylalanine, tyrosine, histidine, methionine, valine, leucine, alanine, phenylglycine, 4-hydroxyphenylglycine, 4-alkoxyphenylglycine and other substituted phenylglycines can be used.

The manner in which the optically Schiff base of the amino-acid amide was formed is not important for the process according to the invention. In addition to the said enzymatic separation of DL-amino-acid amides it is known from, for , U.S. application No. 4,036,852 how to separate DL-phenylglycine amide into optical antipodes via diastereoisomeric salt formation with an optically active 2-pyrrolidone-5-carboxylic acid. Also the undesired antipode obtained in this manner can be racemized with the process according to the invention. Neither is it important for the Schiff base to have the L-form or the D-form.

In a first step of the process according to the invention the optically active Schiff base of the amino-acid amide is dissolved in a water-miscible organic solvent, for instance acetone, methanol or ethanol.

At the same time or later at least 0.05 mole strong base per liter solution is added also, preferably 0.08-1.0 mole/liter, and subsequently the solution is stirred, for instance for 10 minutes to 24 hours. The strong base applied may be, for instance, NaOH, KOH, LiOH, $Ca(OH)_2$ or tetraalkylammoniumhydroxide, in which each of the alkyl groups may contain 1-4 C atoms independently of any of the others. The said tetraalkylammoniumhydroxide can also be used in the form of a strongly basic ion exchanger with free OH groups.

The treatment with base may vary in time, for instance from 10 minutes to 24 hours. Often 15-100 minutes will suffice for racemization of the Schiff base to take place.

The temperature at which the racemization takes place is generally 20°-60° C. If a higher temperature is applied, some byproduct may be formed by hydrolysis and by the formation of diketopiperazine.

In a following step, if further processing to the DL-amino-acid amide is desired, a quantity of acid is added. The addition of acid on the one side serves to neutralize the strong base added and on the other to hydrolyse the Schiff base to form the corresponding salt of the amino-acid amide and the aromatic aldehyde. The acid applied may conveniently be hydrochloric acid or sulphuric acid. By the addition of acid the pH is brought to 3–7, preferably to about 5. The amount of acid is generally equivalent to the total amount of base in the solution, i.e. the amount of Schiff base plus the amount of strong base added.

The temperature in this step is preferably the same as in the preceding step, 20°–60° C. If the temperature rises too high, for instance 100° C., and if the solution is strongly acid, the benzaldehyde compound may be split off and also an undesired saponification of the amide group may take place.

In this step the salt of the DL-amino-acid amide formed precipitates from the solution. This salt is subsequently separated off in the manner known in the art, for instance by filtration.

Finally, the salt is dissolved in water and, using base, the pH is brought to 8–10. The resulting solution is suitable for use in an enzymatic separation of the DL-amino-acid amide.

If an enzymatic separation of DL-amino-acid amides with an enzyme preparation from *Pseudomonas putida* is applied after racemization, preference is given to the use of KOH as base and sulphuric acid as acid, because the enzymatic activity of this preparation is stimulated by potassium ions and by sulphate ions.

In a special mode of realization, the process according to the invention is integrated into the preparation of an L-amino acid starting from the corresponding DL-amino-acid amide. Using an enzyme preparation from *Pseudomonas putida* an aqueous solution of the DL-amino-acid amide is subjected at 20°–60° C. and pH 8–10 to stereospecific hydrolysis to form the L-amino acid, ammonia and the D-amino-acid amide. To this solution, which contains the L-amino acid, ammonia and the D-amino-acid amide, benzaldehyde is added, during which addition a precipitate is formed of the D-N-benzylidene amino-acid amide. After being separated off by filtration or extraction this Schiff base is dissolved in an acetone-water mixture, upon which 0.08–1.0 mole KOH/l solution is added. The solution is now stirred for 1–20 hours at 20°–60° C. After addition of a quantity of $H_2SO_4$ until a pH of 5 has been reached, a precipitate of the sulphuric acid salt of the DL-amino-acid amide is formed. After this salt is separated off and dissolved in water, the DL-amino-acid amide that can again be used in the enzymatic hydrolysis is formed at pH 8–10.

The racemization of an optically active N-benzylidene amino-acid amide can be incorporated also into a process for preparing DL-amino-acid amides from the corresponding DL-aminonitriles, (water-miscible) ketone and strong base (pH 11–14). Such a process is described in GB-A-1548032. Indeed, the reaction conditions described in it to prepare from the DL-aminonitrile the corresponding DL-amino-acid amide are about the same as those at which according to the present invention racemization of the Schiff base takes place. The undesired optical antipode of the amino-acid amide can therefore be converted advantageously into the Schiff base, and the latter can be returned to the step in which the DL-aminonitrile is converted into DL-amino-acid amide. In this step racemization of the optically active N-benzylidene amino-acid amide takes place. A treatment with strong acid, for instance sulphuric acid, then results in the formation of the (sulphuric acid) salt of the DL-amino-acid amide from DL-amino-acid amide (formed from the DL-aminonitrile), as well as from DL-N-benzylidene amino-acid amide (formed according to the mode of realizing the invention described herein). Treatment with KOH at pH 8–10 then yields the DL-amino-acid amide.

The invention is further elucidated hereinafter by means of the following examples.

PREPARATION OF AN OPTICALLY ACTIVE N-BENZYLIDENE AMINO-ACID AMIDE

By way of example a description is given below of the preparation of D-N-benzylidene valine amide. Similarly other starting compounds, to be used in the process according to the invention, can be prepared also.

In a 1-liter reaction flask provided with stirrer, thermometer, cooler, dropping funnel and heating jacket 66 g ammoniumsulphate (0.5 mole) was dissolved at room temperature in 150 ml water and during stirring 250 ml ammonia (25% wt) was added. Subsequently, 65 g potassium cyanide (1.0 mole) and 110 ml water were added. Via the dropping funnel 95 ml isobutyraldehyde (1.0 mole) was subsequently slowly added in drops while ammonia gas was being introduced, at which the temperature did not rise beyond 40° C.

In order to allow this Strecker reaction to terminate the reaction mixture was stirred for 2.5 hours at the temperature obtained. The yield of DL-α-valinonitrile calculated on isobutyraldehyde was 93% according to HPLC analysis.

Subsequently, to this reaction mixture a mixture of 75 ml acetone and 100 ml water was added and the pH was set at 13.3. using 10 ml 8 molar potassiumhydroxide solution. The temperature then rose from 33° C. to 41° C. in 0.5 hour.

This temperature was maintained for 6 hours, upon which 3.0 ml concentrated sulphuric acid was added to neutralize the potassiumhydroxide solution. Then distillation took place. In 1 hour 110 ml of a water-ammonia-acetone mixture was distilled over the top, while the bottom temperature rose to 102° C.

By means of HPLC analysis the yield of DL-α-valine amide was determined. This amounted to 88.4% calculated on the basis of butyraldehyde. The pH of the solution was 9.5. After removal of the potassium sulphate by filtration the solution was brought to 40° C. and 15 g of a preparation containing α-amino acyl amidase, obtained from a strain of *Pseudomonas putida* ATCC 12633, was subsequently added to it. After that the solution was stirred for 20 hours at 40° C.

Subsequently 45 ml benzaldehyde was slowly added to the solution in drops and stirring was continued for 0.5 hour at 40° C.

The precipitated D-N-benzylidene valine amide was filtered off, washed on the filter with 4×75 ml water and dried for 16 hours at 45° C. and at 16 mbar. (From the filtrate L-valine can be recovered).

The yield of dry and (determined by means of thin-layer chromatography) pure D-N-benzylidene valine amide amounted to 82.6 g. The efficiency calculated on the basis of isobutyraldehyde was 40.5% and on the basis of valine amide 91.6%.

From the specific rotation $[\alpha]_D^{20} = -12.7$ (CH$_3$OH; C=2.0) a selectivity of 99.6% could be calculated. These two parameters are defined in example I.

EXAMPLE I

Optically active N-benzylidene amino-acid amide was dissolved in an acetone-water mixture in the amounts stated in table 1 and the resulting solution was subsequently, after the addition of base, stirred for the time stated. Subsequently, while the stirring was continued, an amount of acid (H$_2$SO$_4$ or HCl) was added in drops until a pH of 5 was obtained. After cooling to room temperature the salt of the DL-amino-acid amide formed was isolated by filtration over a glass filter. Subsequent washing took place with acetone (about 3 times the amount by weight of the DL-amino-acid amide salt formed). The yield and the degree of racemization of the tlc-pure (thin-layer chromatography) amino-acid amide salts are also mentioned in table 1. The yield has been calculated as a percentage of the starting quantity in moles. The specific rotation $$[\alpha]_D^{20} = \frac{100 \times \alpha \text{ (measured)}}{1 \cdot c},$$

where l is the length of the polarimeter tube in dm and c the number of grammes of product per 100 ml volume.

The selectivity is expressed as follows:

$$\text{selectivity} = 50\% + \frac{50 \cdot [\alpha]_d^{20} \%}{\text{max. } [\alpha]_D^{20}}$$

In case of pure DL-amino-acid amide the selectivity is 50%.

The maximum $[\alpha]_D^{20}$ of a number of salts of optically active amino-acid amides is mentioned in Greenstein & Winitz, vol. 2, pages 1196–1200, as well as in Beilstein 14 III, page 1489. The following maximum $[\alpha]_D^{20}$ values for the following amino-acid amide salts were found by own observation:

| | | |
|---|---|---|
| D-methionine amide.HCl | −18.2° | (C = 1.0, H$_2$O) |
| D-homophenylalanine amide.sulphate | −15.7° | (C = 1.0, H$_2$O) |
| L-phenylalanine amide.sulphate | +17.8° | (C = 1.0, H$_2$O) |

TABLE 1

Racemization and isolation of amino-acid amide salts

| N-benzylidene compound | solvent | base | temperature °C. | duration in hours | yield amide.salt | spec. rotation $[\alpha]_D^{20}$ ° | selectivity in % |
|---|---|---|---|---|---|---|---|
| 100 m moles D-valine amide | 285 ml acetone + 15 ml water | 3 ml 8 N KOH | 60 | 19 | 90.5% HCl-salt | −0.8 | 51.4 |
| 10 m moles D-leucine amide | 19 ml acetone + 1 ml water | 0.2 ml 8 N KOH | 25 | 24 | 84.1% HCl-salt | −0.2 | 50.9 |
| 1000 m moles D-homophenylanine amide | 1425 ml acetone + 75 ml water | 15 ml 8 N KOH | 45 | 2 | 98.6% sulphate | −0.3 | 51.0 |
| 20 m moles D-methionine amide | 36 ml acetone + 2 ml water | 0.4 ml 8 N KOH | 25 | 3 | 86.7% HCl-salt | −0.1 | 50.3 |
| 50 m moles D-phenylglycine amide | 95 ml acetone + 5 ml water | 1.0 ml 8 N KOH | 20 | 2 | 96.5% HCl-salt | 0.0 | 50.0 |
| 100 m moles L-phenylalanine amide | 190 ml acetone + 10 ml water | 1.0 ml 10 N NaOH | 25 | 2 | 96.7% sulphate | 0.0 | 50.0 |

EXAMPLE II

In the manner described in example I a number of optically active N-benzylidene amino-acid amides were reacemized by incorporating these compounds in an organic solvent, mixed or not mixed with water, and subsequently treating them with an aqueous base solution. Table 2 shows the amounts, racemization conditions, optical rotations and selectivities for these Schiff bases. Unlike example I, no salts of the respective Schiff bases were isolated in example II, but the racemization rate of the Schiff bases itself was examined. After the duration given it was revealed by thin-layer chromatography that there had been no hydrolysis to amino acid and that, moreover, no other products such as, for instance diketopiperazine had been formed.

TABLE 2

| N-benzylidene compound | solvent | base | temperature °C. | duration in min. | α measured in ° | selectivity in % |
|---|---|---|---|---|---|---|
| 2.2 m moles D-phenylglycine amide | 10 ml CH$_3$OH | 0.1 ml 8 N KOH | 25 | 0 | −0.400 | 100.0 |
| | | | | 10 | −0.004 | 50.5 |
| | | | | 15 | −0.002 | 50.2 |
| 2.2 m moles L-phenylalanine amide | 10 ml CH$_3$OH | 0.1 ml 10 N NaOH | 25 | 0 | −10.500 | 100.0 |
| | | | | 15 | −4.250 | 70.2 |
| | | | | 25 | −1.650 | 57.9 |
| | | | | 40 | −0.160 | 50.8 |
| 1.2 m moles | 9 ml acetone | 0.1 ml | 25 | 0 | −0.900 | 100.0 |

TABLE 2-continued

| N-benzylidene compound | solvent | base | temperature °C. | duration in min. | α measured in ° | selectivity in % |
|---|---|---|---|---|---|---|
| D-homophenyl-alanine amide 1.1 m moles | 8 ml acetone + 2 ml water | 0.1 ml 8 N KOH | 25 | 20 | +0.450 | 75.0 |
|  |  |  |  | 40 | +0.190 | 60.6 |
|  |  |  |  | 80 | +0.037 | 52.1 |
| L-tryptophane amide 1.4 m moles | 8 ml acetone + 2 ml water | 0.1 ml 8 N KOH | 25 | 0 | −8.10 | 100.0 |
|  |  |  |  | 30 | −2.16 | 63.3 |
|  |  |  |  | 60 | −0.44 | 52.7 |
| D-methionine amide 2.2 m moles | 10 ml CH$_3$OH | 0.1 ml 8 N KOH | 25 | 0 | −1.77 | 100.0 |
|  |  |  |  | 15 | +0.36 | 60.2 |
|  |  |  |  | 30 | +0.05 | 51.4 |
| L-histidine amide 4.4 m moles | 9 ml CH$_3$OH | 1.0 ml tetramethyl ammoniumhydroxide (10 gew. %) | 25 | 0 | −5.270 | 100.0 |
|  |  |  |  | 2 | −2.160 | 70.5 |
|  |  |  |  | 6 | −0.525 | 55.0 |
|  |  |  |  | 12 | −0.150 | 51.4 |
| L-phenyl-alanine amide | 20 ml CH$_3$OH + 0.2 ml H$_2$O | 1 g. Dowex I in OH-form | 25 | 0 | −11.430 | 100.0 |
|  |  |  |  | 30 | −2.413 | 60.6 |
|  |  |  |  | 60 | −0.524 | 52.3 |
|  |  |  |  | 75 | −0.295 | 51.3 |

COMPARATIVE EXAMPLE 1

To 50 mmoles D-N-benzylidene homophenylalanine amide 50 ml water and 5 mmoles KOH were added. A suspension of the said optically active compound in water was formed. This suspension was stirred for 24 hours at 25° C. After filtration and drying it was found that there had been no racemization. Apparently the Schiff base must be soluble in order to be capable of being racemized.

COMPARATIVE EXAMPLES 2–3

In a flask 2.2 mmoles L-phenylglycine amide was dissolved in 10 ml methanol resp. 8 ml acetone with 2 ml water. In the manner described in example II base was added and the optical rotation was measured at intervals. The results are given in table 3. They show that without the form of a Schiff base there is no racemization of the optically active phenylglycine amide. They also show that, as a potential imine-forming agent, acetone does not induce racemization, or hardly so, in other words that acetone only serves as solvent.

COMPARATIVE EXAMPLE 4

Of a solution of 2.2 mmoles D-N-benzylidene phenylglycine amide in 10 ml methanol the optical rotation was determined, without the addition of base, after 0 minute, 10 minutes and 30 minutes. It was found to be −0.401°, −0,400° and −0.410° respectively. Consequently, there had been no racemization. This experiment shows that addition of base is essential for racemization.

COMPARATIVE EXAMPLES 5–6

In the manner described in comparative example 4 the racemization of D-N-benzylidene-phenylalanine amide was carried out in the presence of the weak bases of ammonia resp. triethylamine. Table 4 shows that these bases are not strong enough to effect the racemization.

TABLE 4

| N-benzylidene compound | solvent | base | temperature °C. | duration in min. | α measured in ° | selectivity in % |
|---|---|---|---|---|---|---|
| 2.2 m moles L-phenylalanine amide | 10 ml CH$_3$OH | 0.1 ml concentrated ammonia | 25 | 0 | −10.338 | 100.0 |
|  |  |  |  | 60 | −9.543 | 96.2 |
| 2.2 m moles L-phenylalanine amide | 10 ml CH$_3$OH | 0.14 ml triethylamine | 25 | 0 | −10.415 | 100.0 |
|  |  |  |  | 60 | −10.273 | 99.3 |
|  |  |  |  | 180 | −9.933 | 97.7 |

COMPARATIVE EXAMPLE 7

A solution of 4.0 g D-N-benzylidene-phenylglycine amide in 400 ml toluene was boiled (112° C., atmospheric pressure) for 20 hours while being stirred continuously. At the times stated a sample was taken to

TABLE 3

| Compound | solvent | base | temp. °C. | duration in min. | α measured in ° | selectivity in % |
|---|---|---|---|---|---|---|
| 2.2 m moles L-phenylglycine amide | 10 ml CH$_3$OH | 0.1 ml 8 N KOH | 25 | 0 | +2.150 | 100 |
|  |  |  |  | 10 | +2.130 | 99.5 |
|  |  |  |  | 70 | +2.110 | 99.1 |
| 2.2 m moles L-phenylglycine amide | 8 ml acetone 2 ml H$_2$O | 0.1 ml 8 N KOH | 25 | 0 | +2.180 | 100 |
|  |  |  |  | 10 | +2.140 | 99.5 |
|  |  |  |  | 60 | +1.930 | 94.3 | determine the rotation. These measured α-values are shown in table 5. They show that no thermal racemization took place.

TABLE 5

| time in hours | α measured in ° | selectivity in % |
|---|---|---|
| 0 | −0.044 | 100 |
| 2 | −0.045 | 100 |
| 4 | −0.044 | 100 |
| 20 | −0.044 | 100 |

We claim:

1. A process for the preparation of DL-amino-acid amide from the corresponding DL-aminonitrile in the presence of water and a water-miscible ketone and at least 0.05 mole of strong base per liter solution while in the same step incorporating the racemization of a corresponding optically active N-benzylidene amino-acid amide.

* * * * *